United States Patent

Lassila et al.

[11] Patent Number: 5,719,307
[45] Date of Patent: Feb. 17, 1998

[54] DIAMINE CHAIN EXTENDERS AND METHOD OF USE

[75] Inventors: Kevin Rodney Lassila, Kutztown; Jeremiah Patrick Casey, Emmaus, both of Pa.

[73] Assignee: Air Products and Chemicals, Inc., Allentown, Pa.

[21] Appl. No.: 646,190

[22] Filed: May 7, 1996

Related U.S. Application Data

[63] Continuation-in-part of Ser. No. 555,199, Nov. 8, 1995, abandoned, which is a continuation-in-part of Ser. No. 226,916, Apr. 13, 1994, abandoned.

[51] Int. Cl.$^6$ ....................... C07C 205/57; C07C 224/60
[52] U.S. Cl. ............................................ 560/20; 560/50
[58] Field of Search ..................................... 560/20, 50

[56] References Cited

U.S. PATENT DOCUMENTS

| | | | |
|---|---|---|---|
| 3,188,302 | 6/1965 | Lorenz | 260/77.5 |
| 3,428,610 | 2/1969 | Klebert | 260/75 |
| 3,736,350 | 5/1973 | Meckel et al. | 260/471 R |
| 3,846,351 | 11/1974 | Huffaker et al. | 260/2.5 AM |
| 3,926,923 | 12/1975 | Preston | 260/29 |
| 3,932,360 | 1/1976 | Cerankowski et al. | 260/77.5 AM |
| 4,218,543 | 8/1980 | Weber et al. | 521/51 |
| 4,222,955 | 9/1980 | Chung et al. | 260/465 F |
| 4,283,549 | 8/1981 | Holm | 560/50 |
| 4,476,318 | 10/1984 | Harada et al. | 560/50 |
| 4,737,527 | 4/1988 | Maranci | 523/205 |

FOREIGN PATENT DOCUMENTS

| | | |
|---|---|---|
| 0013956 | 2/1980 | European Pat. Off. |
| 2419322 | 4/1973 | Germany |
| 2419322 | 11/1980 | Germany |
| 5781445 | 11/1980 | Japan |

OTHER PUBLICATIONS

Baron, et al. "On the Use of Trimethylene Glycol Di-p-aminobenzoate as a Curing Agent for Polyurethane Elastomers." *J Appl. Polym. Sci.* 20, pp. 285–286 (1976).

Zey. "Esterification." *Kirk–Othmer Encyc. of Chem. Tech.* Third Ed.; John Wiley & Sons; New York. vol. 9, pp. 291–310 (1980).

*Primary Examiner*—Robert Gerstl
*Attorney, Agent, or Firm*—Mark L. Rodgers

[57] ABSTRACT

Polyurethane-urea elastomers are made using as a chain extender 2-methyl-1,3-propanediol-bis-p-aminobenzoate which is the reduction product from hydrogenating 2-methyl-1,3-propanediol-bis-p-nitrobenzoate. The latter composition is preferably made by esterifying p-nitrobenzoic acid and 2-methyl-1,3-propanediol using a stoichiometric excess of the diol initially, adequate to render the reaction mixture processible, and after converting to a nonvolatile form sufficient diol to form diester with substantially all of the acid, removing free diol by distillation while continuing the esterification of unreacted acid and transesterification of monoester formed to diester. This process, which can be applied broadly to esterification of other nitroaromatic acids with other aliphatic diols, produces high yields of diester without needing extraneous solvent for processibility and with only water as a by-product. The 2-methyl-1,3-propanediol-bis-p-aminobenzoate exhibits reactivity and processing characteristics which make it a suitable drop-in replacement for MoCA in polyurethane-urea elastomer manufacture.

2 Claims, No Drawings

DIAMINE CHAIN EXTENDERS AND METHOD OF USE

CROSS-REFERENCE TO PARENT APPLICATION

This is a continuation-in-part of application Ser. No. 08/555,199, filed 8, Nov., 1995, which is a continuation-in-part of application Ser. No. 08/226,916, filed 13 Apr., 1994, both now abandoned the subject matter of both which is hereby incorporated by reference.

FIELD OF THE INVENTION

This invention relates to an aromatic diamine useful as a chain extender in the manufacture of polyurethane-ureas. In another aspect it relates to an intermediate p-nitrobenzoate. In yet another aspect it relates to a method of curing polyurethane compositions with an aromatic diamine and to the resulting product, and in still another aspect it relates to a process for making aromatic diamines by esterification of nitroaromatic acids with diols.

BACKGROUND OF THE INVENTION

Polyurethane-urea elastomers are widely used in industry to fabricate molded products. These elastomers are typically formed by reacting an organic polyisocyanate with a compound having a molecular weight between 400 and 10,000 containing at least two Zerewitenoff active hydrogen atoms, such as a polyhydroxyl compound, and an aromatic diamine chain extending agent. Alternatively, the chain extender is reacted with an isocyanate-terminated polyurethane prepolymer. Such prepolymers are well known in the art. In the molding operation the rate of reaction of the chain extender, or curative, and the processibility of the reacting composition is critical. If the reaction proceeds too fast, the composition will set up or gel before the mold can be completely filled. On the other hand, if the reaction is too slow, cycle times become too long and the cost of the operation is excessive. Finding the right curative for polyurethane-urea elastomers in a particular molding operation has been the subject of intensive research in this field for many years.

Three techniques have been used to reduce the reactivity of aromatic diamines in order to produce polyurethane-urea elastomer molding formulations with improved processibility. One technique involves incorporating organic substituents on the aromatic ring to hinder sterically the amine functionality. Klebert, U.S. Pat. No. 3,428,610 (1969) and Weber et al., U.S. Pat. No. 4,218,543 (1980) describe taking this approach to the problem, the latter patent also discussing the importance of reaction rates in the so called "one-shot" reaction injection molding (RIM) systems where the polyisocyanate, polyhydroxyl compound and aromatic polyamine are all combined at once rather than using a prepolymer.

A second technique involves adding an alkyl substituent to the amine nitrogen which both sterically hinders the amine group and reduces the number of active hydrogens. An example of this approach is given by Huffaker et al, U.S. Pat. No. 3,846,351 (1974) with N,N'-dialkyl-p-phenylenediamine.

The third technique for reducing activity of an aromatic diamine is through electronic deactivation of the ring. Meckel et al., U.S. Pat. No. 3,736,350 (1973) take this approach by introducing ester and halogen or alkoxy groups onto the ring.

Lorenz, U.S. Pat. No. 3,188,302 (1965) describes a diamine curative which takes advantage of both steric hindrance and electronic deactivation to reduce its reactivity. Representative of such material is 4,4'-methylene-bis(2-chloroaniline) which has been widely used in the art and is known by its shorthand name "MoCA". MoCA has the additional advantage of remaining liquid for long periods in the supercooled state even though it has a relatively high melting point of 130° C. This enhances its processibility. Unfortunately, as pointed out by Baron et al., J. Appl. Polym. Sci., 20, pp.285–6 (1976) the Occupational Safety and Health Administration has placed MoCA on a list of suspected carcinogens thereby stimulating considerable research for a suitable "drop-in" replacement. Several candidates are described by Baron et al. and in a related patent of Cerankowski et al., U.S. Pat. No. 3,932,360 (1976) as alkylene glycol di-p-aminobenzoates. These curatives are made by reacting p-nitrobenzoyl chloride with an alkylene or cycloalkylene diol followed by reduction of the nitro groups to amine. Preferably the diol contains an odd number of carbons, and more preferably 3 or 5 carbons. All species are said to possess reasonable supercooling properties with the best candidate compared with the commercial MoCA being 1,3-propanediol di-p-aminobenzoate. The curative derived from 1,2-propanediol is said to have given poor elastomers and was not a good MoCA substitute. Baron et al. further concluded that the reduced reactivity of these compounds is attributable to electronic rather than steric effects.

The search to replace MoCA, which for some molding operations is considered too slow, is illustrated by the '543 patent cited above and by Chung et al., U.S. Pat. No. 4,222,955 (1980) who describe diamino alkylbenzoates, alkylbenzonitriles and alkylene bis(amino alkylbenzoates) as polyurethane curatives which are slower reacting than prior aromatic diamines but faster than MoCA which frequently requires a catalyst to shorten its reaction time.

Finding a suitable MoCA replacement in order to meet safety and health concerns is made more difficult by environmental problems associated with manufacturing such a replacement. The process described for making the curatives of the '360 patent, for example, generates hydrochloric acid or amine hydrochlorides which introduce corrosion, environmental and disposal problems. In addition, the reaction is conducted in a mutual solvent for the diol and p-nitrobenzoyl chloride and this requires recovery and recycling steps for an efficient operation. Japanese Patent Publ. No. 57-81445 (1982) describes making a bis (aminobenzoate) diester by reacting a dihalide, an amino benzoate and a base, while Harada et al., U.S. Pat. No. 4,476,318 (1984) disclose making 1,3-propanediol bis(p-aminobenzoate) by reacting a p-aminobenzoic acid alkali metal salt with dihalogenated propane in an aprotic polar solvent. Both of these processes produce halide-containing waste streams and the latter requires solvent separation and recovery for commercial practicability. An attempt to avoid these problems as described by Holm, U.S. Pat. No. 4,283, 549 (1981) involves esterification of nitro-benzoic acid and diols in a melt followed by dissolving the product in a solvent sparingly soluble in water, such as anisole, and reducing the nitro groups to amine. Holm recognizes that production of the monoester is undesirable and deals with this problem by using a stoichiometric excess of the acid in the esterification in order to drive the reaction to the diester. At the end of the esterification unreacted acid is converted to its sodium salt by adding water and sodium carbonate. This salt is soluble in water but sparingly soluble in anisole. The operation is complex and requires leaching, separation and recovery of both the organic acid and solvent.

Preston, U.S. Pat. No. 3,926,923, discloses high molecular weight polymers prepared by reacting at least one aromatic dicarboxylic acid halide and at least one aromatic diamine having preformed ester units. Included in the list of diamines useful in the reaction is 2,2-dimethyl-1,3-propane-bis(p-aminobenzoate). This, along with several other alkylene bis(aminobenzoates) are disclosed in German patent abstract 2419322. Additionally, Maranci, U.S. Pat. No. 4,737,527, discloses heat curable compositions which contain amine-functional curing agents, including 2,2-dimethyl-1,3-propanediol-bis-p-aminobenzoate. None of the diamines disclosed, however, include those of the present invention which we found exhibit superior results as chain extenders.

It might appear that direct esterification of p-aminobenzoic acid with a diol would be the ideal solution since the only reaction by-product is water. Esterification of carboxylic acid and alcohol is an equilibrium reaction typically driven by carrying out the reaction in an excess of alcohol or by continuously removing water as it is produced either by distillation, as an azeotrope, or with a desiccant, as discussed by Zey, in *Kirk-Othmer Encyclopedia of Chemical Technology*, Third Edition; John Wiley & Sons; New York, 1980; Vol. 9, pp 291–310. In diester production use of excess diol during the reaction is unacceptable since the monoester would be the primary product. On the other hand, use of excess carboxylic acid to consume the diol and form more diester creates processing problems because of the high melting point of the acid and difficulties associated with removal of excess acid from the desired product. Using stoichiometric equivalents of organic acid and diol in a melt and forcing the reaction by removal of water is disclosed in European Patent Appl. No.0 013 956 B1 (1980), but this operation is complicated by the physical form of the reaction mixture which is difficult to process.

SUMMARY OF THE INVENTION

We have found that a species of organic diamine within the generic description of diamines found in the '360 patent, cited above, is surprisingly superior to other known diamines as a chain extender useful as a drop-in replacement for MoCA in the production of polyurethane-urea elastomers. This organic diamine is the novel composition 2-methyl-1,3-propanediol-bis-p-aminobenzoate which is not specifically named or suggested in the prior art. It is made by hydrogenation of its precursor, 2-methyl-1,3-propanediol-p-nitrobenzoate, which is also a novel compound useful as the intermediate from which the diamine is formed. This chain extender is used to react with an organic polyisocyanate and a compound having a molecular weight between 400 and 10,000 and containing at least two Zerewitenoff active hydrogen atoms in the production of cast polyurethane-urea elastomers. The chain extender (or curative) can also be reacted with a polyurethane prepolymer containing terminal isocyanate groups to form the urea linkages in the cured product. The processibility of the diamine and its reactivity rate with isocyanate groups make it especially attractive for molding large items.

Another aspect of our invention is the preferred method of making the diamine curative which is the reaction of 2-methyl-1,3-propanediol in stoichiometric excess with p-nitrobenzoic acid in an esterification which produces high yields of the desired diester that can then be reduced by hydrogenation of the nitro groups present to amine. This process can be applied more broadly to obtain high yields of nitroaromatic diesters, particularly p-nitrobenzoate diesters, with aliphatic diols having 2 to 12 carbon atoms. The excess diol in the process greatly facilitates processibility of the reaction mixture so that solvents are not required. As soon as sufficient diol has reacted with acid to form product including monoester, thereby becoming relatively nonvolatile, free diol is removed from the reaction mixture by distillation. Water by-product of the esterification is also removed in the same manner. "Sufficient diol" is that amount which is necessary to form the diester with substantially all of the nitroaromatic acid that is to be reacted. The esterification is then continued driving the reaction to completion, that is, production of the diester by both esterification with unreacted acid and by transesterification of monoester to form diester and diol, which is removed as it is formed, by reduced pressure if necessary.

This procedure which physically manipulates the presence and absence of diol during the esterification does not require a solvent, produces no by-products other than water and provides very high yields of the desired diester.

DETAILED DESCRIPTION OF THE INVENTION

The composition 2-methyl-1,3-propanediol-bis-p-aminobenzoate is useful as a chain extender or curative in production of cast polyurethane-urea elastomers. The formulations cured with this material have exhibited working times unexpectedly far longer than those cured with the bis-p-aminobenzoates of the prior art. In addition, this material exhibits processibility superior to that of previously prepared bis-p-aminobenzoates in terms of diminished propensity to crystallize from the melt. Coupled with the desirable physical properties of the elastomer product, these advantages make the organic diamine of our invention a prime candidate as a drop-in replacement for MoCA in current industrial molding operations. Particularly noteworthy is the formation of an extremely strong yet soft elastomer using commercially available prepolymers.

The preferred method of making 2-methyl-1,3-propane-bis-p-aminobenzoate first forms the intermediate p-nitrobenzoate by mixing together under esterification conditions p-nitrobenzoic acid and a stoichiometric excess of 2-methyl-1,3-propanediol. The excess diol used is not only more than that required on an equivalent basis to react with all of the p-nitrobenzoic acid, but it is also adequate to render the reaction mixture processible and thereby obviate the need for extraneous solvent. It has been found that about 1 to 5 mols of diol per mol of acid works very well in this respect, but somewhat less diol can be used depending upon the conditions chosen for the reaction. The use of greater amounts of diol does not adversely affect the reaction but it does reduce reactor capacity, which is an important consideration for industrial operations.

The esterification reaction is carried out until sufficient diol needed to convert substantially all of the acid to the diester has reacted to form a relatively nonvolatile product which includes monoester of the acid and diol. At this point the reaction mixture typically contains unreacted acid and diol, monoester, diester and water by-product. This is an easily processible mixture. Surprisingly, removal of both diol and water from this mixture does not reduce significantly its processibility but results in very high yields, on the order of 90%, of the desired diester. The diol can be removed by distillation, if necessary under subatmospheric pressures. At the beginning the excess diol greatly enhances the processibility of the reaction mixture obviating use of an added solvent which would present recovery and recycle problems. By the time diol is removed from the reaction mixture, sufficient ester has been formed that the diol is no longer needed for this function. Although at the outset the excess diol drives the reaction toward production of the monoester, by removing diol after the esterification has progressed as described, high yields of diester are obtained through further esterification of remaining starting acid and transesterification of monoester with loss of diol. In this way use of a solvent is avoided, there are no by-products other than water, the reaction mixture remains readily processible throughout, and the reaction vessels are used efficiently with high productivity and high yields of the desired product. The nitro groups on this product are then hydrogenated to amine groups resulting in the diamine chain extender of the invention.

This esterification process has broader application than in the production of 2-methyl-1,3-propanediol-bis-p-aminobenzoate and, in fact, can be used advantageously to prepare a broad class of dicarboxylate esters of nitroaromatic acids and aliphatic diols. For example, the nitroaromatic acid can contain other substituents which do not interfere with the esterification reaction, such as halogen or alkyl and aryl groups. Benefits of the process invention can be enjoyed whenever the nitroaromatic acid has a relatively high melting point making it difficult to process but the diol with which it is to be reacted is fluid under the reaction conditions and consequently can serve the function of a process solvent or reaction medium ensuring efficient contact between reactants and catalyst. Preferably the nitroaromatic acid is p-nitrobenzoic acid and the diol is an alkylene or cycloalkylene diol having 2 to 12 carbon atoms. Such esters can be represented by the structural formula:

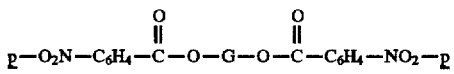

wherein G is an alkylene or cycloalkylene group containing 2 to 12 carbons. The nitro groups in the compounds represented by this formula can be converted to amine groups by hydrogenation using well known techniques to provide the desired diamines useful as chain extenders in the production of polyurethane-urea elastomers.

The esterification reaction is carried out in the presence of a catalyst and at elevated temperatures which are sufficient to complete the reaction in a reasonable time without decomposition of reactants or products. Generally the temperatures are in the range of 50° to 200° C., and preferably above 100° C. The pressure of the reaction is usually atmospheric, but can be regulated to obtain the desired rate of distillation removal of water and diol depending upon the particular diol being used and the reaction temperature.

The catalysts useful in esterification reactions are well known in the art and include compounds such as mineral acids, for example, sulfuric or hydrochloric acid, tin salts, organo-titanates, silica gel, cation-exchange resins, sulfonic acids such as benzenesulfonic acid and p-toluenesulfonic acid, phosphoric acid, and the like. A preferred catalyst is titanium (IV) isopropoxide because it has been found that this catalyst results in fewer by-products. Strong Bronsted acids such as Amberlyst®-15 which is a strongly acidic, macroreticular resin manufactured by Rohm and Haas Co., Nafion® NR50, a strongly acidic perfluorinated ion exchange resin manufactured by E.I.du Pont de Nemours & Co., or methane sulfonic acid are catalysts which produce esters rapidly but also cause oligomerization of the diol to form an unwanted by-product. This problem can be addressed by lowering the reaction temperature.

Diols suitable for use in the esterification are aliphatic diols having 2 to 12 carbon atoms. Examples include 1,3-propanediol, 1,5-pentanediol, 2-methyl-1,3-propanediol, 1,3-butanediol, 2,3-butanediol, 1,4-cyclohexanediol, 3-chloro-1,2-propanediol, 1,12-dodecanediol, ethylene glycol, 2-ethyl-2-methyl-1,3-propanediol, 1,6-hexanediol, 1,8-octanediol, 1-phenyl-1,2-ethanediol, 2,2,4,4,-tetramethyl-1,3-cyclobutanediol, and the like. The alkylene and cycloalkylene diols are preferred.

Procedures well known in the art for making and molding the polyurethane-urea elastomers can be used with the diamine chain extenders provided by our invention. The following examples are presented to illustrate specific embodiments of our invention and should not by construed to limit the scope of our invention unduly.

EXAMPLE 1

This example illustrates a preferred procedure for making 2-methyl-1,3-propanediol-bis-p-nitrobenzoate.

A two liter three-necked round-bottomed flask equipped with distillation takeoff head and nitrogen bubbler was charged with 2-methyl-1,3-propanediol (269.68 g, 2.99 mol) and titanium (IV) isopropoxide (50.38 g, 0.18 mol). The mixture became cloudy when the catalyst was added. The contents of the reactor was heated in an oil bath at 65° C. and 4-nitrobenzoic acid (500.14 g, 2.99 mol) was added forming a processible slurry. The temperature of the bath was increased to 170° C., and nitrogen was bubbled through the mixture. Water began to distill from the vessel even before the oil bath had reached the set temperature. After about 30 minutes, diol was observed in the distillate. After 5.5 hours, a sample analyzed by gas chromatography showed that the reaction mixture contained diester and monoester in a weight ratio of 82.2/17.5 with no additional materials other than starting materials evident. Heating was continued for an additional 15 hours after which the ratio of diester to monoester had increased to 92.2/7.5. The product was cooled to 126° C. and 800 mL of mixed xylenes was added. The resulting solution was filtered hot and cooled to room temperature with stirring. The crystallized product was collected by vacuum filtration and dried overnight (80° C., 12 in. Hg) to afford 465 g (80.3% yield) of product which had a melting point of 122°–125° C. with a gas chromatographic (GC) assay of 96.8% diester and 3.1% monoester. Identity of the product was confirmed by $^1$H and $^{13}$C NMR and electron impact and chemical ionization mass spectrometry.

EXAMPLE 2

This example illustrates hydrogenation of p-nitrobenzoate which can be prepared as described in Example 1 to form the corresponding diamine useful in polyurethane-ureas as a chain extender.

A two liter autoclave was charged with water-covered Raney® nickel (25 g), absolute ethanol (950 mL), and 2-methyl-1,3-propanediol-bis-p-nitrobenzoate (303.9 g). The reactor was sealed and pressure checked with nitrogen, purged three times with nitrogen and then three times with hydrogen, and pressured to about 50 psi with hydrogen. The contents of the autoclave was heated to 50° C. and the hydrogen pressure increased to 500 psi. Heat of reaction increased the temperature to 80° C. where it was maintained with an internal cooling coil. After hydrogen uptake ceased (about 50 minutes), the reaction mixture was cooled to room temperature. The catalyst was removed by filtration through Celite®, an analytical grade filter agent composed of diatomaceous earth (Celite Corporation). Absolute ethanol was used to aid the transfer. The filtrate was concentrated to 900 mL and the solution allowed to cool to room temperature and placed in an ice water bath. The resulting solid was collected by vacuum filtration and dried to constant weight in a vacuum oven to afford 165.1 g of product having a melting point of 124°–126° C. An additional 55.1 g of crude product was isolated by evaporation of the solvent after recrystallization of the solid from the mother liquor. Highly purified product obtained by recrystallization from absolute ethanol had a melting point of 125°–126° C. Product identity was confirmed by elemental analysis and by $^1$H and $^{13}$C NMR.

EXAMPLE 3

This example illustrates that other diols can be used in the preferred esterification process of this invention and that the equilibrium of the reaction can be driven toward diester production by removal of excess diol under vacuum during the latter part of the reaction.

The diol (60 mmol) was weighed into a 100 mL round-bottomed flask. Catalyst (10% by weight based on the acid) was added. The flask was fitted with a distillation head and the contents heated to 60° C. 4-Nitrobenzoic (60 mmol) was then added and the temperature raised to 170° C. Water began to condense overhead when the temperature reached 160° C. indicating that the esterification was under way. At a later point in the reaction diol removal was initiated while keeping the reaction mixture fluid and processible. At the end of four hours, the pressure in the flask was decreased to about 400 torr while continuing to remove diol. After 8 hours, heating was discontinued and the products were analyzed by GC. The results set forth in Table 1 show that the composition of the product was about 90% dibenzoate with the rest monobenzoate and unidentified by-product resulting mainly from diol oligomerization.

TABLE 1

| Diol | Catalyst | GC Analysis* | | |
|---|---|---|---|---|
| | | Monoester | Diester | Others |
| 1,3-Propanediol | Ti(IV) isopropoxide | 4.4 | 94.9 | 0.7 |
| 1,5-Pentanediol | Ti(IV) isopropoxide | 10.0 | 89.9 | 0.1 |
| 2-Methyl-1,3-propanediol | Amberlyst-15 | 5.7 | 93.9 | 0.4 |

*Flame ionization detector area percent

EXAMPLE 3

Several comparative runs were made to screen catalysts, temperature, and reaction stoichiometry and to show results obtained when excess diol is not removed during the course of the reaction.

The catalyst screening runs were made by charging to a 25 mL two-necked round bottomed flask equipped with a magnetic stirrer, reflux condenser, and nitrogen inlet 2-methyl-1,3-propanediol (17.7 g, 190 mmol) and catalyst (0.5 g). This mixture was heated to 60° C. and 4-nitrobenzoic acid (6.35 g, 38 mmol) added after which the mixture was heated to 175° C. Samples were taken at 1, 4, 6 and 22 hours into the reaction and analyzed by gas chromatography (GC) using flame ionization detector area percent for the approximate weight percent of each component after normalizing out unreacted diol present. Results are given in Table 2.

TABLE 2

| Catalyst | Time | Weight Percent | | | |
|---|---|---|---|---|---|
| | | Acid | Monoester | Diester | Others |
| Amberlyst-15 | 1 | 0.0 | 95.0 | 0.0 | 4.8 |
| | 4 | 0.0 | 89.4 | 4.0 | 6.3 |
| | 6 | 0.0 | 89.0 | 3.6 | 7.2 |
| | 22 | 0.0 | 70.8 | 4.5 | 24.1 |
| Titanium(IV) isopropoxide | 1 | 3.0 | 97.0 | 0.0 | 0.0 |
| | 4 | 1.1 | 86.2 | 11.5 | 0.0 |
| | 6 | 0.9 | 88.1 | 10.8 | 0.0 |
| | 22 | 0.9 | 90.6 | 8.3 | 0.0 |
| Nafion | 1 | 0.0 | 87.5 | 6.1 | 6.1 |
| | 4 | 0.0 | 79.2 | 4.1 | 16.5 |
| | 6 | 0.0 | 75.4 | 5.4 | 18.9 |
| | 22 | 0.0 | 61.2 | 3.8 | 34.2 |
| Methane Sulfonic Acid | 1 | 0.0 | 69.5 | 7.6 | 21.6 |
| | 4 | 0.0 | 64.1 | 5.2 | 26.9 |
| | 6 | 0.0 | 61.2 | 4.4 | 31.2 |
| | 22 | 0.0 | 48.9 | 2.4 | 45.5 |

The data of Table 2 show that the nitrobenzoic acid reacts rapidly to form esterification products in the presence of all the catalysts examined. Titanium (IV) isopropoxide is preferred because it produces the least amount of oligomerized by-products. With the other catalysts the reaction is complicated by oligomerization of the diol which accounts for a significant amount of the "Others" reported in Table 2. It is also apparent that without removal of excess diol according to the invention, production of the desired diester is quite low.

In additional runs using Amberlyst-15 catalyst, production of oligomerized by-products was eliminated by reducing the reaction temperature to 115° C. As a consequence, however, conversion of acid to ester within the time frame of 1 to 6 hours was significantly lower.

Formation of a processible mixture at the outset of the reaction requires the use of either solvent or excess diol. Using a solvent has the obvious disadvantage of introducing recycle or disposal problems to an industrial operation. As shown by the Table 2 data, excess diol drives the reaction toward monoester production. In the procedure of the invention, however, the starting carboxylic acid is reacted sufficiently to trap enough diol as an esterification product in the reaction mixture to convert substantially all of the acid to the diester when the reaction is driven to completion. Once this amount of diol is rendered nonvolatile, the free diol is removed by distillation and the esterification continues by reaction of the monoester with unreacted carboxylic acid to liberate water and by transesterification of monoester to diester with liberation of diol.

Reaction stoichiometry is important because if too much diol is used at the beginning of the reaction, reactor productivity is decreased. But if not enough diol is present, processibility is inadequate. In screening runs with Amberlyst-15 or titanium (IV) isopropoxide as the catalyst (10% by weight based on the acid), 4-nitrobenzoic acid and 2-methyl-1,3-propanediol as the reactants in molar ratios of 0.5:1, 1:1, 2:1 and 5:1, diol to acid, and a reaction temperature of 173° C., it was found that the 1:1 molar ratio provided the best balance between processibility and reactor productivity, although higher ratios were also practicable. The 0.5:1 ratio, which represents the stoichiometric requirement for diester production, was not suitable owing to high viscosity of the reaction mass making it difficult to process.

Although the process of Examples 1 and 2 represents the preferred method of making 2-methyl-1,3-propanediol-bisp-aminobenzoate, this novel chain extender can also be made by other methods, as illustrated by Example 4.

EXAMPLE 4

A three liter three-necked round-bottomed flask equipped with nitrogen inlet, condenser, thermocouple, overhead stirrer, and addition funnel was charged with 4-nitrobenzoyl chloride (654.2 g, 3.53 mol) and pyridine (850 mL). A slight exotherm, heating the reaction mixture to 54° C., was noted. The reaction mixture was heated to 74° C., whereupon all of the solids in the reaction vessel dissolved. At this point 2-methyl-1,3-propanediol (161.7 g, 1.77 mol) was added to the reaction solution via the addition funnel over a period of 18 minutes. The color of the reaction mixture changed from a deep yellow to a light brown and the exotherm of the reaction heated the solution to 130° C. The reaction mixture was heated to reflux for five hours, cooled slightly, and poured onto 2 liters of ice, aiding the transfer by addition of water. The resulting solid was collected by suction filtration, washed thoroughly with water, and dried with suction to provide 871.1 g of crude product. This material was recrystallized from 2500 mL of toluene (hot filtration) to provide 527.9 g of 2-methyl-1,3-propanediol-bis-p-nitrobenzoate having a melting point of 125°–126° C. Identity of the product was confirmed by elemental analysis, by $^1H$ and $^{13}C$ NMR, and by chemical ionization mass spectrometry.

The nitrobenzoate ester was then converted to the diamine by hydrogenation as described in Example 2.

The following Examples 5 through 11 compare the novel chain extender of this invention with closely related commercial chain extenders of the prior art to demonstrate the surprising and unexpected advantages of the invention.

EXAMPLE 5

The reactivity of 2-methyl-1,3-propanediol-bis-p-aminobenzoate was compared to that of Polacure® 740M which is 1,3-propanediol-bis-p-aminobenzoate, a product of Air Products and Chemicals, Inc. The procedure for potlife evaluation was that described by Casey et al., *Proceedings of the SPI 28th Annual Technical/Marketing Conference*, pp 218–223 (1984). This test was performed by dissolving the chain extender (1 eq.) in CAPA® 200, a polycaprolactone of 274 equivalent weight from Interox (1 eq.), in a stainless steel cup and preconditioning this mixture at 50° C. for one hour. The homogeneity of this mixture was ascertained, and Adiprene® L167, a toluene diisocyanate (TDI) capped 1000 molecular weight polytetramethyleneglycol from Uniroyl (2 eq.), thermostatted at 50° C. was carefully layered on top. The test cup was placed in a thermostatted block on the test apparatus and a perforated plunger driven at constant pressure by a reciprocating air motor was activated. Frequency data for the plunger were stored on a minicomputer and later converted to relative viscosity. A plot of relative viscosity vs time was produced and the time required for the mixture to reach a relative viscosity of 5000 ($t_{5000}$) was determined. This is a value which provides a concise reactivity comparison for various chain extenders.

The results of the above evaluations showed that in the initial stages of the reaction, a period of about 20 to 25 minutes, the viscosities of the formulations increased at a rate which was essentially independent of the chain extender used. At this point the viscosity of the composition being cured with the 1,3-propanediol derivative of the prior art exhibited an abrupt rise, moving quickly to a $t_{5000}$ value of 29 minutes, and a viscosity above 10,000 within another minute. In sharp contrast, the viscosity of the composition being cured with the 2-methyl-1,3-propanediol derivative continued to increase at the same rate to completion of the reaction, reaching a $t_{5000}$ value of 48 minutes, which is very close to the 42 minute potlife of MoCA. This result indicates that the chain extender of this invention could be used as a replacement for MoCA in industrial production with a minimum of operational adjustments.

The observed difference in cure profiles of these two aminobenzoate chain extenders was quite unexpected because the reactivity, and hence the potlife, of the aminobenzoate of the prior art is said to be mainly a function of the electronic nature of the molecule (see Baron, et al. supra). Merely placing a methyl substituent symmetrically on the propylene group linking the p-aminobenzoates in the molecule would not be expected to impact so heavily the cure profile of the chain extender. In addition to enhancing its value as a replacement for MoCA, this extended cure profile for the product of the invention enables longer working times in large molding operations and provides greater flexibility in such industrial applications.

EXAMPLE 6

This example compares the melt stability of the two p-aminobenzoates compared in Example 5. Cast elastomers prepared with solid chain extenders are commonly made by adding the molten chain extender to an isocyanate prepolymer. A key parameter for determining the processibility of the chain extender is the temperature at which the molten chain extender begins to crystallize, for when this occurs, processing is considerably complicated. Thus, a chain extender which remains liquid, even when supercooled, is more processible.

Samples of 1,3-propanediol-bis-p-aminobenzoate and 2-methyl-1,3-propanediol-bis-p-aminobenzoate were each placed in capillary tubes and heated to 135° C. in a Thomas-Hoover oil immersion melting point apparatus. At this point, heating was discontinued, and the time was recorded. After 5 minutes, the oil temperature had reached 90° C. and 1,3-propanediol derivative was beginning to form crystals while the 2-methyl-1,3-propanediol derivative remained molten. After 6 minutes, the temperature had reached 81° C. and all of the 1,3-propanediol-linked material had crystallized but the 2-methyl-1,3-propanediol-linked compound had not. After 25 minutes, the temperature had decreased to 40° C. and still no transition to a solid had occurred for the composition of the invention.

Thus, it has been shown that 2-methyl-1,3-propanediol-bis-p-aminobenzoate remains substantially liquid even when cooled over 80° C. below its normal melting point. Supercooling properties was one of the advantages pointed out by the '360 patent for the compositions disclosed, and since the 1,3-propanediol-linked derivative was the compound most preferred, it was not expected that the 2-methyl-1,3-propanediol-linked derivative of this invention would be so markedly superior in this respect. The chain extender of this invention, therefore, exhibits surprisingly enhanced processibility.

EXAMPLE 7

Accurately weighed samples of 1,3-propanediol-bis-p-aminobenzoate and 2-methyl-1,3-propanediol-bis-p-aminobenzoate were placed in pans for differential scanning calorimetry. The pans were placed in the DSC apparatus and the temperature was adjusted to 100° C. The temperature was then increased at a rate of 2° C. per minute to 150° C. The temperature was then decreased at a rate of 1° C. per minute to 25° C., and then increased again to 150° C. at a rate of 2° C. per minute.

Both compounds exhibited a melting endotherm upon initial heating. During the first cooling 1,3-propanediol-bis-p-aminobenzoate exhibited a crystallization exotherm at 90° C., but no crystallization exotherm was observed for the 2-methyl-1,3-propanediol-bis-p-aminobenzoate even on cooling to room temperature. Both samples were then reheated to 150° C. at a rate of 2° C. per minute. The 1,3-propanediol derivative exhibited a second melting endotherm at 128° C. No endotherm was observed during the second heating of the sample of the 2-methyl-1,3-propanediol derivative, confirming that none of the sample had recrystallized from the melt.

These results show that 2-methyl-1,3-propanediol-bis-p-aminobenzoate produces a much more stable melt than the 1,3-propanediol derivative of the prior art. This property for the diamine of the invention considerably simplifies processing as a polyurethane-urea elastomer chain extender because once melted it remains molten at temperatures below its melting point for a considerable period of time.

EXAMPLE 8

Often in cast polyurethane-urea manufacture, a solid diamine chain extender is dissolved in a polyether or polyester diol to simplify handling and enhance processibility. The dissolution process is typically performed by heating a mixture of the diamine chain extender and the polyol until it becomes homogeneous. If, when this solution is cooled, the diamine chain extender begins to crystallize or precipitate, casting is complicated. Further, since the crystallized material is unlikely to react efficiently, an article of poor quality will probably be formed.

In order to compare the behavior of the composition of the invention with that of the prior art when dissolved in polyol, two 10 mL vials were charged with PolyTHF650, a polytetramethylene glycol of 650 molecular weight manufactured by BASF (1.08 g) and either 1,3-propanediol-bis-p-aminobenzoate (1.05 g) or 2-methyl-1,3-propanediol-bis-p-aminobenzoate (1.09 g). Both mixtures were heated until they were homogeneous and then allowed to cool under ambient conditions. The temperature was monitored by means of a thermocouple immersed in each mixture. The results are summarized in Table 3.

TABLE 3

| Linking Group | Time (min) | Temp (°C.) | Observations |
| --- | --- | --- | --- |
| 1,3-propanediol | 0 | 160 | Homogeneous solution |
| | 7 | 41 | Some solid present |
| | 16 | 28 | Additional solid |
| | 34 | 26 | Still more solid |
| | 91 | 26 | Abundant crystals |
| | 180 | Ambient | Complete crystallization |
| 2-methyl-1,3-propanediol | 0 | 155 | Homogeneous |
| | 15 | 29 | Homogeneous |
| | 32 | 27 | Homogeneous |
| | 89 | 26 | Homogeneous |
| | 1 day | Ambient | Minor crystal formation |
| | 4 days | Ambient | Complete crystallization |

The above reported results showed that the diamine chain extender of this invention exhibited a much lower rate of recrystallization than the prior art material, thereby having superior processibility.

EXAMPLE 9

The minimum temperature at which crystal formation can occur in a mixture of polyol and diamine chain extender is also important since this determines an appropriate storage temperature and provides a temperature above which processing problems are not likely to occur. The diamine chain extenders and the PolyTHF650 used in Example 8 were mixed in the same ratios and heated in an oil bath until the chain extenders dissolved (130° C.). The temperature of the bath was successively decreased in 5° C. increments and allowed to stand at that temperature for a period of 30 minutes. Once the temperature at which crystal formation was evident had been determined, the samples were slowly heated to the minimum temperature at which they again became homogeneous. The temperature was oscillated between these crystallization-solution regimes until the minimum temperature at which the samples were homogeneous and the maximum temperature at which crystals could be observed was determined.

For the 1,3-propanediol-bis-p-aminobenzoate, at 123° C. crystals were observed after one hour while at 124° C. the solution was homogeneous.

For the 2-methyl-1,3-propanediol-bis-p-aminobenzoate, at 100° C. crystals were observed after about 24 hours while at 105° C. the solution was homogeneous. These tests again showed that the diamine chain extender of the invention exhibits superior processibility.

EXAMPLE 10

This example compares physical properties of polyurethane-urea elastomers using the chain extender of the invention with elastomers using commercial chain extenders, including MoCA. Plaques were cast by mixing neat molten chain extender (1.0 equivalent) with prepolymer (1.05 equivalents) at 70° C. and placing the mixture in a mold having inside dimensions of 6 in.×6 in. by ⅛ in. after the mold had been preheated to 100° C. The material was then pressed at 100° C. and about 15 tons and cured in the mold until the part had developed sufficient mechanical strength to be removed (about 1 hour). The elastomer was then postcured at 100° C. for a period so that the total cure time was 16 hours. Defect-free pieces were cut from these plaques and their properties were measured according to ASTM procedures D-412-83 (Microtensile), D-624-81 (Die C Tear), and D-2240-81 (Durometer Hardness). The results are given for each elastomer in Table 4. Elastomers made from three different prepolymers were evaluated, and each prepolymer was cured with 2-methyl-1,3-propanediol-bis-p-aminobenzoate and at least one commercial chain extender. Group A elastomers were made with Adiprene® L167, group B with Airthane® PET 95A (a TDI-capped 1000 molecular weight polytetramethylene glycol containing less than 0.1% free TDI, manufactured by Air Products and Chemicals, Inc.), and group C were made with Airthane® PET 70D (a TDI-capped 650 molecular weight polytetramethylene glycol containing less than 0.1% free TDI, manufactured by Air Products also). In Table 4, the elastomers cured with the diamine of the invention are indicated by (1), those cured with 1,3-propanediol-bis-p-aminobenzoate (Polacure® 740M) by (2), those cured with MoCA by (3), and an elastomer cured with Ethacure® 300 (a chain extending agent of 80% 3,5-di(methylthio)-2,4-toluenediamine and 20% 3,5-di(methylthio)-2,6-toluenediamine obtained from Ethyl Corporation) indicated by (4).

TABLE 4

| Elastomer | Hardness Sh.A | Sh.D | Tensile Strength (PSI) 100% | 200% | 300% | Break | Elongation (at break) | Tear Die C |
|---|---|---|---|---|---|---|---|---|
| A (1) | 80 | 35 | 310 | 500 | 760 | 4190 | 660% | 160 |
| A (2) | 81 | 41 | 270 | 400 | 590 | 2320 | 750% | 90 |
| B (1) | 90 | 42 | 640 | 1200 | 2400 | 7490 | 520% | 290 |
| B (2) | 97 | 49 | 1770 | 2330 | 3080 | 5110 | 480% | 650 |
| B (3) | 97 | 48 | 2030 | 2690 | 3800 | 4510 | 360% | 600 |
| B (4) | 95 | 55 | 2610 | 3520 | 4920 | 5250 | 330% | 460 |
| C (1) | 100 | 70 | 3610 | 5130 | na | 6490 | 280% | 980 |
| C (3) | 97 | 67 | 4990 | 6080 | na | 6560 | 240% | 1080 |

The data of Table 4 show that when either Adiprene® L167 or Airthane® PET 95A was used as the prepolymer, the curative of the invention provided elastomers (A1 and B1 ) which were softer but stronger at break than the elastomers obtained with these prepolymers cured with 1,3-propanediol-bis-p-aminobenzoate (A2 and B2) or the other chain extenders (B3 and B4). This combination of properties is unusual and unexpected. Such a combination of high strength and softness is of particular value in articles like tires and paper rollers.

When Airthane® 70D was the prepolymer, the chain extender of the invention produced an elastomer with properties comparable to those obtained with MoCA. The excellent physical properties coupled with the fact that the processibility was similar to that of MoCA means that 2-methyl-1,3-propanediol-bis-p-aminobenzoate is more nearly a drop-in replacement for MoCA than other prior art chain extenders. This result is quite surprising when one considers that 1,3-propanediol-bis-p-aminobenzoate (Polacure®) was introduced as an alternative to 1,4-methylene-bis-ortho-chloroaniline (MoCA), the industry standard chain extender for polyurethane-urea cast elastomers. The potential for the composition of this invention, meanwhile, went undetected and unappreciated.

EXAMPLE 11

Runs were carried out to compare the performance of 2,2-Dimethyl-1,3-propanediol-bis-p-aminobenzoate as a chain extender with that of the compound of the present invention.

Preparation of 2,2-Dimethyl-1,3-propanediol-bis-p-nitrobenzoate. The procedure used was that outlined in U.S. Pat. No. 3,932,360 [Cerankowski, et al.]. To a 500 mL three-necked round-bottomed flask equipped with overhead stirrer, heating mantle, condenser, and nitrogen inlet were added 4-nitrobenzoyl chloride (74.22 g, 0.40 moles), 2,2-dimethyl-1,3-propanediol (20.83 g, 0.2 mol) and pyridine (100 mL). The reaction was heated to reflux with stirring for 5 hours, and then cooled to room temperature. The resulting slurry was added to 1500 mL of water and stirred for ca. 30 minutes. The solid product was collected by suction filtration, and then stirred overnight in 1 L of water. The product was again collected by filtration, washed with 2×200 mL of water, air dried in the filter for 1 h, then dried in a vacuum oven overnight (91° C., 13.2 in Hg, slight $N_2$ purge through oven) to afford 75.96 g of pale tan powder (mp 147.9°–148.3° C.) identified as 2,2-dimethyl-1,3-propanediol-bis-p-nitrobenzoate by nuclear magnetic resonance (NMR) spectroscopy.

Preparation of 2,2-Dimethyl-1,3-propanediol-bis-p-aminobenzoate. The diamine was prepared by hydrogenation (55° C. and 550 psig) of the dinitro compound (10.0 g) in the presence of 10% Pd-C catalyst (0.5 g) in 50 mL of tetrahydrofuran. Gas uptake stopped about 20 minutes after reaching the reaction temperature. The reaction mixture was cooled and the catalyst was removed by filtration. The solvent was removed and the residue was recrystallized from ca. 75 mL of absolute ethanol to afford 6.0 g of off-white solid (mp 162°–164° C.). The product was identified as 2,2-dimethyl-1,3-propanediol-bis-p-aminobenzoate by nuclear magnetic resonance spectroscopy.

Melt Stability of 2,2-Dimethyl-1,3-propanediol-bis-p-aminobenzoate. The procedure of Example 6 above was repeated using the subject material. When a sample of 2,2-dimethyl-1,3-propanediol-bis-p-aminobenzoate was heated, the material did not melt until the temperature reached 162°–164° C. When heating was discontinued, the temperature dropped to 113° C. in 4 minutes, and the material began to crystallize. After about an additional minute, the temperature had reached 107° C., and the material had completely crystallized. The transition from the melt to the solid occurred at a temperature of nearly 30° C. higher than the corresponding transition for 1,3-propanediol-bis-p-aminobenzoate, the compound identified as preferred in the prior art. Crystallization from the melt at this temperature makes this material unsuitable for use as a chain extender in cast polyurethane-ureas.

Differential Scanning Calorimetry of 2,2-Dimethyl-1,3-propanediol-bis-p-aminobenzoate. A procedure similar to that of Example 7 above was performed. Note, however, that because of the high melting point of this compound, the sample had to be heated to 180° C., rather than the 150° C. used in the other experiments.

An accurately-weighed sample of 2,2-dimethyl-1,3-propanediol-bis-p-aminobenzoate was placed in a pan for differential scanning calorimetry. The pan was placed on the DSC apparatus and the temperature was adjusted to 100° C. The temperature was then increased at a rate of 2° C. per minute to 180° C. The temperature was then decreased at a rate of 1° C. per minute to 25° C., and then increased again to 180° C. at a rate of 2° C. per minute.

The compound exhibited a melting endotherm of 116 J/g during the first heating at a temperature of 165° C. No clear crystallization exotherm was observed upon cooling. However, when the sample was reheated, two crystallization exotherms (70 J/g at about 73° C. and 1 J/g at about 82° C.) were observed. Continued heating resulted in the observation of a crystallization endotherm (116 J/g) at 163° C.

The magnitude of the melting endotherm was 116 J/g for both the first and second heatings, indicating that the product had completely recrystallized prior to the second melting. Further, the sum of the heat released during the crystallization exotherms (70 J/g) was significantly lower than the melting endotherms, indicating that the material had partially crystallized when cooled to room temperature.

Use of this product as a chain extender in polyurethane-urea cast elastomer manufacture would be difficult because of the high temperatures required to reach a molten state. Even if equipment capable of heating this material to the melt were available, processing would be complicated by the fact that a significant amount of crystallization occurs during cooling. This behavior is to be contrasted to that of the diamine of this invention which melts at a lower temperature and exhibits no crystallization from the melt when cooled to room temperature.

Crystallization from Polyol. The procedure of Example 8 above was repeated with 2,2-dimethyl-1,3-propanediol-bisp-aminobenzoate (1.01 g) and PolyTHF650 (1.01 g). The following data were obtained:

| Linking Group | Time (min) | Temp (°C.) | Observations |
|---|---|---|---|
| 2,2-dimethyl-1,3-propanediol | 0 | 160 | Homogeneous |
| | 2 | 134 | Solids visible |
| | 4 | 95 | Complete crystallization |

The above results clearly show that the performance of this chain extender is inferior to the 2-methyl-1,3-propanediol-bis-p-aminobenzoate of the present invention.

Other advantages and features of our invention will be apparent to those skilled in the art from the foregoing disclosure without departing from the spirit or scope of our invention.

We claim:

1. 2-methyl-1,3-propanediol-bis-p-aminobenzoate.
2. 2-methyl-1,3-propanediol-bis-p-nitrobenzoate.

\* \* \* \* \*